United States Patent [19]

Chang

[11] 4,200,561
[45] Apr. 29, 1980

[54] STABLE, COMPATIBLE THIXOTROPIC GEL WITH COPOLYMER GELLING AGENT

[75] Inventor: Irving B. Chang, Morristown, N.J.

[73] Assignee: Allied Chemical Corporation, Morris Township, Morris County, N.J.

[21] Appl. No.: 925,252

[22] Filed: Jul. 17, 1978

[51] Int. Cl.² .................. C09G 1/10; C09G 1/16; C09K 3/20

[52] U.S. Cl. ................. 260/23 H; 260/29.6 H; 260/31.2 R; 260/33.4 R; 260/33.6 PQ; 260/33.6 UA; 260/DIG. 47; 424/78; 424/81; 424/83

[58] Field of Search .......... 260/23 H, 29.6 H, 31.2 R, 260/33.4 R, 33.6 PQ, 33.6 UA, DIG. 47; 424/78, 81, 83

[56] References Cited

U.S. PATENT DOCUMENTS

| | | | |
|---|---|---|---|
| 3,658,741 | 4/1972 | Knutson et al. | 260/29.6 H |
| 3,660,333 | 5/1972 | Kremer | 260/23 H |
| 3,759,674 | 9/1973 | Gregg | 44/7 C |
| 3,891,587 | 6/1975 | Watts | 260/23 H |
| 3,909,280 | 9/1975 | Dench et al. | 106/271 |
| 4,020,228 | 4/1977 | Eastes | 260/23 H |
| 4,104,216 | 8/1978 | Clampitt | 260/23 H |

*Primary Examiner*—Ronald W. Griffin
*Attorney, Agent, or Firm*—Alan M. Doernberg; Jay P. Friedenson

[57] ABSTRACT

A stable, compatible thixotropic gel of the type gelled from a mixture including a solvent, a cosolvent and a gelling agent. The gelling agent comprises a copolymer of ethylene and at least one comonomer selected from the group consisting of acrylic acid, methacrylic acid, ethacrylic acid, esterified acrylic acid, vinyl acetate, vinyl formate, vinyl propionate and mixtures thereof. The copolymer has a number average molecular weight between about 500 and about 10,000.

35 Claims, 11 Drawing Figures

STABLE, COMPATIBLE THIXOTROPIC GEL WITH COPOLYMER GELLING AGENT

BACKGROUND OF THE INVENTION

Gels are used for a variety of products having cosmetic, medicinal, veternary, paint, printing and other applications. In many such applications, thixotropic gels are preferred, having the property of being semisolid colloids (gels) when undisturbed, but flowing readily when shaken, stirred, sheared or otherwise subjected to stress. Such gels typically are prepared by mixing a solvent, cosolvent, gelling agent (also called gellant) and optionally additional oils and waxes, active ingredients, preservatives, pigments or other coloring matter and other additives under conditions in which the mixture is either a liquid solution or a suspension. The mixture is then cooled causing a gel to form, accompanied in some instances by polymerization or other reaction between various substituents. The final gel is a semisolid suspension. It should be appreciated, however, that only some gels so formed are stable and exhibit good thixotropy, with many gels so formed either separating with time (being too thin) or not yielding to shear (being too thick). It should also be appreciated that many mixtures of components fail to form or retain a colloidal state such that droplets of one or more components (typically an oil or wax) separates upon cooling so as to form an unstable or grainy material which is unsatisfactory for many applications.

In the production of such gels, particularly in cosmetic gels such as lipsticks and deodorant and antiperspirant sticks, the gelling agent is frequently carnauba wax, candellela wax, beeswax or other organically derived waxes which contain a mixture of paraffins, fatty esters, fatty alcohols and sometimes fatty acids. Such gelling agents are often inconsistent from one batch to the next, requiring extra care in formulating cosmetic products. Such waxes also have relatively low melting points such that gels having such waxes become liquid and flow when warmed to about 50° C. or above. Often gellants such as paraffin, insect and microcrystalline waxes suffer from the same defects, as do the synthetic organophillic bentonite gellants, such as those referred to by the tradename Quarternium-18 Hectorite, used by the cosmetic industry.

Thus a need exists for a gelling agent of consistent quality which can form stable, compatible thixotropic gels with common solvents, cosolvents and other additives of the type now used in thixotropic gels.

BRIEF DESCRIPTION OF THE INVENTION

The present invention includes a stable, compatible thixotropic gel having in the oil phase between about 5 and about 60 weight % gellant, between about 5 and about 50 weight % of a solvent incompatible at room temperature with the gellant and between about 20 and about 90 weight % of a cosolvent compatible with both the gellant and the solvent, at least 25 weight % of said gellant being a copolymer having between about 40 and about 96 mole % ethylene monomer and between about 4 and about 60 mole % of comonomer selected from the group consisting of acrylic acid, methacrylic acid, ethacrylic acid, esterified acrylic acid, vinyl acetate, vinyl formate, vinyl propionate and mixtures thereof, said copolymer having a number average molecular weight between about 500 and about 10,000, said copolymer being present in a proportion great enough to maintain said gel composition stable from 10° to 50° C.

DETAILED DESCRIPTION

The present invention is concerned with gels having a novel gelling agent and exhibiting thixotropy and stability as discussed herein. These gels are preferably without substantial color contribution from the gelling agent; but it should be appreciated that in certain applications, such as deodorant sticks, the colorlessness of the gelling agent is not as critical as in other applications such as lipsticks. It should also be appreciated that the gellant may contribute to the sheen of the gel.

The term "compatible" is used herein to mean that at room temperature of 15°–25° C., the gel does not separate into visibly distinct phases or become visibly grainy because of the gellant crystallizing out in microscopic particles. Compatibility is easily determined by forming a mixture of gel components at elevated temperatures, such as 70°–100° C., and cooling the mixture to room temperatue with stirring. Incompatible mixtures will show droplets or grains when pressed between two microscope slides or exhibit excessive cloudiness compared to compatible gels.

The term "stable" is used herein to mean that the gel does not readily flow in the absence of shear, such as when a container of gel is turned on its side. "Stable" is also meant to include a gel remaining compatible throughout the range of 10° to 50° C. (and preferably over a broader temperature range). Gels with insufficient amounts of the present copolymers will separate or flow, especially at temperatures of 30°–50° C., since the quantity of gellant microcrystals will be insufficient to maintain the gel structure. If, as is normally the case, the gellant particles are denser than the solvent or cosolvent, then a liquid layer may form with time on top of the gel evidencing instability of the type referred to herein as a gel being "too thin". As explained below, it is possible to make certain gels stable by exchanging some normally solid solvent or cosolvent for part of the normally liquid solvent or cosolvent in an unstable gel composition. Such exchanges are only preferred for compositions relatively close in proportions of copolymer, solvent and cosolvent to to stable gels.

The term "thixotropic" is used herein in its normal meaning of spreading or flowing with stress, but remaining stable in the absence of stress. It should be appreciated, however, that very thick gels which spread only with difficulty are unsuitable for many applications. For example, within the range of about 5-60 weight % gellant in the oil phase, gels with over about 30 weight % copolymer are usually too stiff for many cosmetic, veterinary and medicinal applications. Such gels may, however, be suitable in applications such as deodorant sticks where substantial stress is desirable to cause spreading of the gel.

The weight percentages of solvent, cosolvent and gellant are stated in terms of the oil phase only. It should be appreciated that many gels of the present type have only a single liquid phase (considering the solid microcrystalline gellant particles as part of the oily liquid phase in which they are dispersed). Other gels may be of the oil in water or water in oil type, generally with one or more surfactants used to disperse the discontinuous phase in the continuous phase. The present gel compositions are preferably either of a single oil phase or of the oil in water type (the oil being the discontinuous phase).

In computing the percentage of gellant, solvent and cosolvent in the oil phase it should be recognized that various additives or surfactants; may also be present in or primarily in the oil phase. In such systems, it is intended that all such additives which are compatible with the gellant be considered a part of the cosolvent and that all such additives which are incompatible with the gellant be considered a part of the solvent. Surfactant components which are more hydrophillic than hydrophobic additive associate primarily with the water phase should be disregarded.

Furthermore, the amount of gellant may be a function of the type of copolymer used and the solvent. For example the vinyl ester copolymers and the lower acid number copolymers (under about 50 acid number) are preferably used at 5–25 weight % of the oil phase with a relatively hydrophobic solvent such as castor oil, peanut oil and the like. Such gels may be one phase of an oil in water emulsion. Such formulations are often cosmetic creams or the like. Higher acid copolymer (50–100) are preferably used at 10–40 weight % or even higher of the oil phase, usually the oily phase present, with a relatively hydrophillic solvent as propylene glycol, polyethylene glycol of low monomer number or the like. Such formulations are often medicinal or veterinary creams with an active ingredient soluble or easily dispersed in the hydrophillic solvent.

The gelling agent of the invention may be any of a variety of ethylene copolymers. Suitable copolymers and methods for their preparation are described in U.S. Pat. Nos. 3,658,741 to Knutson et al. (issued Apr. 25, 1972) and 3,909,280 to Seven et. al. (issued Sept. 30, 1975). Ethylene copolymers satisfying the present criteria are also known and in many cases commercially available materials.

The copolymer has a number average molecular weight, as generally understood in the polyethylene art, between about 500 and about 10,000 with those between about 1000 and about 5000 being preferred. More preferred is a number average molecular weight between about 2000 and about 4000, with certain preferred embodiments having average molecular weights about 2000, about 3000, about 3200 and about 3500.

The several unsaturated acid monomers (acrylic, methacrylic and ethacrylic acids) may be incorporated into the copolymer during polymerization, as may the vinyl esters (vinyl acetate, vinyl formate and vinyl propionate). Esterified acrylic acid monomers are produced by polymerizing acrylic acid with ethylene and the partially or completely esterifying the copolymer product with an alcohol such as methanol, ethanol, propanol, isopropanol, butanol, isobutanol, t-butanol or higher alcohols up to about 22 carbons. It is also preferred that such acid copolymers be only partially esterified, such as down to an acid number of about 5–10.

The ethylene copolymer gellant need not be the sole gellant or sole oil phase gellant employed. Thus beeswax, carnauba wax or other organically derived waxes of the type conventionally employed in thixotropic gels may be used in conjunction with the ethylene copolymer. It is preferred, however, especially in gels which are relatively thin by virtue of the low proportion of gellant (under 10% of the oil phase), that such other waxes be used in relatively minor proportions such as less than 50% by weight of the copolymer gellant.

The copolymer gellants are almost inevitably mixtures by the nature of their polymerization, but the present invention also contemplates mixtures of separately prepared copolymers such as an ethylene-acrylic acid copolymer mixed with an ethylene-vinyl acetate copolymer. Homopolymer ethylenes may also be employed in combination with described copolymers.

The proportion of ethylene compared to comonomer in the copolymer is not critical although a broad range of about 40–90 mole % ethylene is suitable. It is preferred, however, that at least about 1–50 mole % of the copolymer be one or more comonomers. The several esters named as comonomers are preferably present at between about 1 and 50 mole %, with about 5 to about 30 mole % being more preferred and between about 5 and about 20 mole % being most preferred. The several unsaturated acids named as comonomers are preferably present in proportions giving an acid number (in mg KOH/g) between about 30 and about 150, with between about 30 and 80 being more preferred.

The gels of the present invention are preferably prepared by heating and mixing the ingredients together under a homogeneous solution results. Solution temperature, depending on composition can be in the range of 70°–130° C. The gels are then cooled fast with agitation. This forces the polyethylene to crystallize out in very fine particle size. If the gel favors large crystal growth, fast cooling keeps the crystals from growing further and the gels are generally thixotropic, opaque, and stable. Slow cooling of these gels could normally result in a coarse, unstable gel. With quick cooling, these crystals are so small in particle size that when this gel is pressed between two glass plates in a thin film, they are transparent and therefore no longer reflect light.

It has been found, however, that when other normally solid materials are present in addition to the copolymer gellant, such as other gellants (for example beeswax) or such as a normally solid cosolvent (for example stearic alcohol), that slower cooling is possible without loss of stability.

Thixotropic gels are a highly desirable form for personal care products to be marketed in. This is because when the crystals are fine and are held quiescent, they interlock to give the gel a firm structure, but when shear is applied, the structure breaks down and the gel spreads easily. When the gel is very translucent, the copolymer crystals are very fine, then fast cooling is often not required and the gel is less thixotropic. Therefore, for a personal care product, there is a trade-off between opacity with thixotropy, or, sheen and translucency with less thixotropy. Nevertheless, gels of the present type that exhibit even limited thixotropy are within the scope of the invention.

Gels prepared from mixtures of a single solvent, a single cosolvent and a single gellant (a copolymer) which are themselves stable and neither "too thin" nor "too thick" are preferred. Those component gels which are "too thin" may also be improved by substitution of a thicker solvent or a solid cosolvent for a portion of the existing material. Similarly, gels which are "too thick" can be improved by use of an emollient oil, ester or even mineral oil in place of some of the solvent to make the gel less thick. It is preferred, however, to begin with a three component gel in or near the range of "interesting" gels before making the above substitutions.

EXAMPLES 1-11

In each of the following examples, the three ingredients shown in the Figures were heated and mixed in a glass beaker until a homogenous solution resulted. Solution temperatures ranges from about 85° to about 130°

C. The mixtures were then cooled by placing the beaker in a cold water bath and agitating as the gel formed. Fast cooling keeps the crystal size of the copolymer small. A sample of the cooled product was then placed between microscope slides and held up to a light. A clear film was an indication of compatibility. Excessive cloudiness or graininess was taken as an indication that the mixture was incompatible.

In each example several points were selected on the ternary diagram designed to delineate the line between compatible and incompatible mixtures. Another group of points were selected to delineate the line between "interesting" gels of the type that are stable and spread easily and other gels which are either too thick or too thin. This determination was somewhat subjective, but corresponds in general to the property of not separating when held at 50° C. for one or more days. It should be appreciated, however, that, since mixtures of gellant, solvent and cosolvent which are only somewhat "too thin" or "too thick" can be improved by varying other ingredients, the present invention is not limited to the "interesting" range as measured for these three primary components.

EXAMPLE 1

Figure 1:
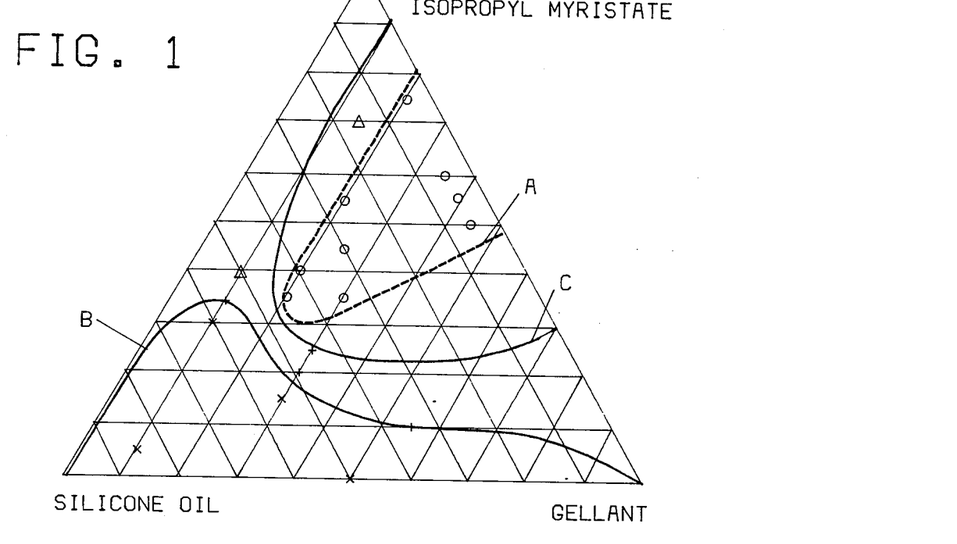

22 gels were prepared by the method described above using as solvent Dow 556 fluid (a polyphenylmethylsiloxane oil available from Dow Chemical Corporation having the properties: 22.5 centistokes viscosity at 25° C., specific gravity of 0.90 at 25° C., 1.460 refractive index at 25° C., 127° C. flash point and acid number of 0.1 mgKOH/g) and as cosolvent isopropyl myristate. The gellant was an ethylene-vinyl acetate copolymer having 14 mole % vinyl acetate, a softening point of 95° C., a Brookfield viscosity at 140° C. of about 500 centipoises and a number average molecular weight about 3500 (from Allied Chemical Corporation as A-C Polyethylene Copolymer 400). Based upon these 22 points, a region bounded by line A in FIG. 1 was determined to contain the "interesting" or stable thixotropic gels (as shown by o's) and the region below line B determined to contain the incompatible mixtures (as shown by x's) which became excessively cloudy or grainy on cooling. An exemplary "interesting" gel was formed from 45 weight percent copolymer, 15 weight percent polyphenylmethylsiloxane oil and 40 weight percent isopropyl myristate. The remaining region above line B was determined to contain gels which were either undesirably too thick (as shown by +'s) or undesirably too thin (as shown by triangles). It should be appreciated, however, that gels with compositions only slightly outside of the region bounded by line A may be suitable for some applications and hence are not excluded from the present invention, although they are not preferred. Line C is drawn to include these compatible gels which are only marginally either too thin or too thick in addition to the "interesting" gels. Gels between line A and C can be made "interesting" by substitution of solvent or cosolvent.

EXAMPLE 2

Figure 2:
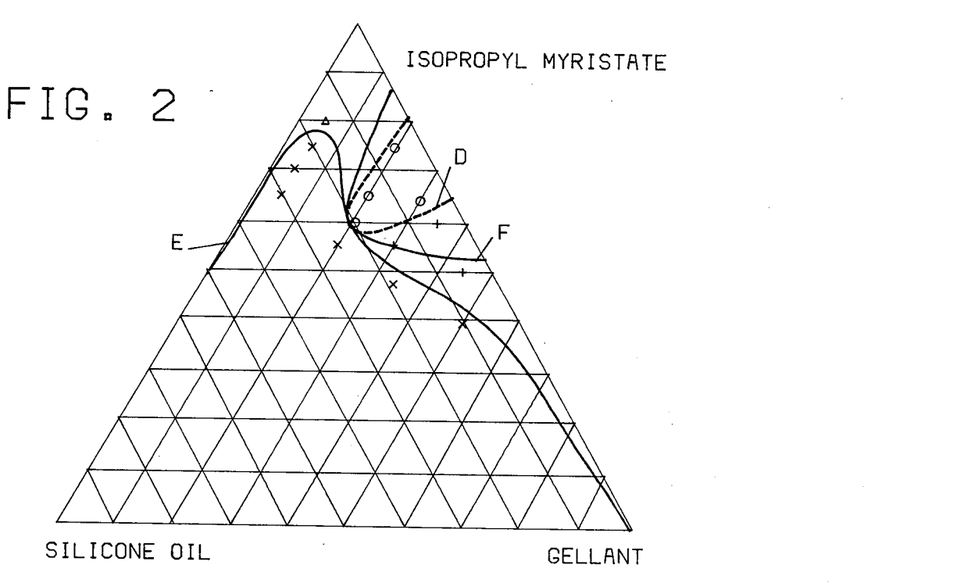

Following the procedure described above, 16 gels were prepared using as solvent Dow 200 fluid-350 cs (a dimethyl siloxane polymer available from Dow Chemical Corporation having the properties: 350 centistokes viscosity at 25° C., 0.970 specific gravity at 25° C. 1.403 refractive index at 25° C. and 315° C. flash point), as cosolvent isopropyl myristate and as gellant the same ethylene-vinyl acetate copolymer as in Example 1. The results are displayed in FIG. 2 using the same symbols as in FIG. 1. The region bounded by line D was determined to contain the "interesting" gels as in Example 1 and the region below line E was determined to contain the incompatible mixtures as in Example 1. As in Example 1, line F further includes gels marginally either too thin and marginally too thick gels.

EXAMPLE 3

Figure 3:
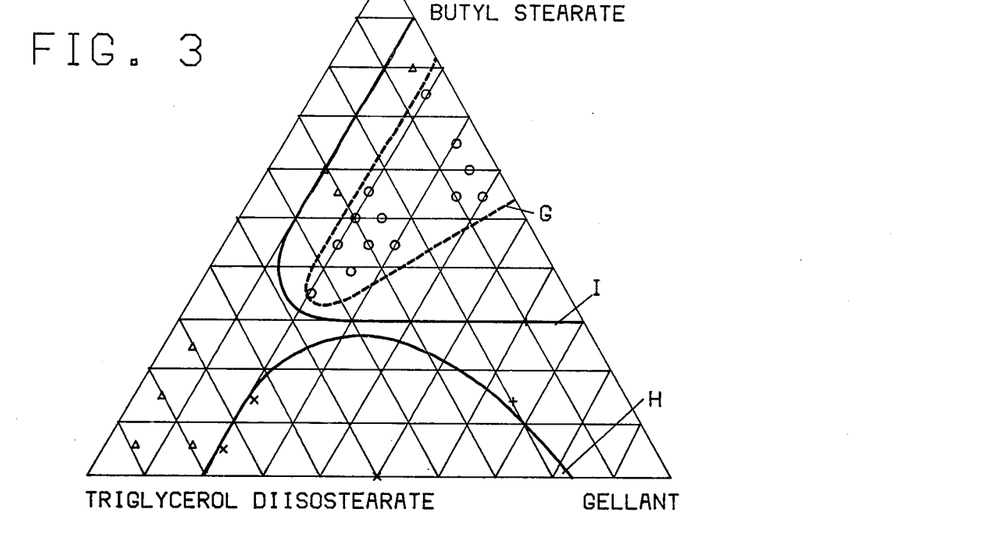

Following the procedure described above, 28 gels were prepared using as solvent triglycerol diisostearate (from Malmstrom Division of Emery Industries who has recommended its use in cosmetic gels), as cosolvent butyl stearate and as gellant the same ethylene - vinyl acetate copolymer as in Example 1. The results are displayed in FIG. 3 using the same symbols as in FIG. 1. The region bounded by line G was determined to contain the "interesting" gels as in Example 1 and the region below line H was determined to contain the incompatible gels as in Example 1. Line I has been drawn to further include gels marginally either too thin or too thick.

EXAMPLE 4

Figure 4:
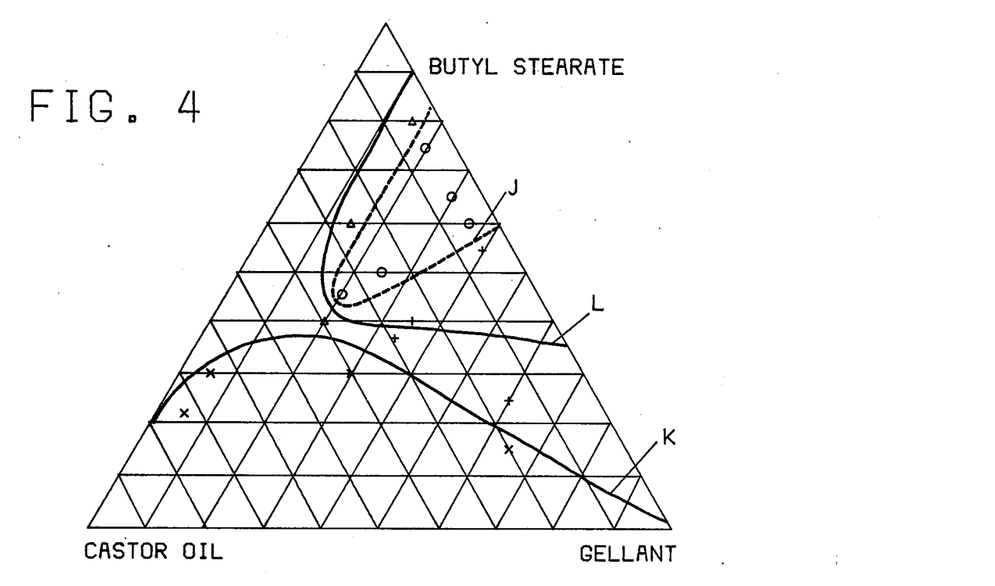

Following the procedure described above, 16 gels were prepared with castor oil as solvent, butyl stearate as cosolvent and the same ethylene - vinyl acetate copolymer as in Example 1 as gellant. The results are displayed in FIG. 4 using the same symbols as in FIG. 1. The region bounded by line J was determined to contain the "interesting" gels as in Example 1 and the region below line K was determined to contain the incompatible mixtures as in Example 1. Line L has been drawn to further include gels marginally either too thin or too thick.

EXAMPLE 5

Figure 5:
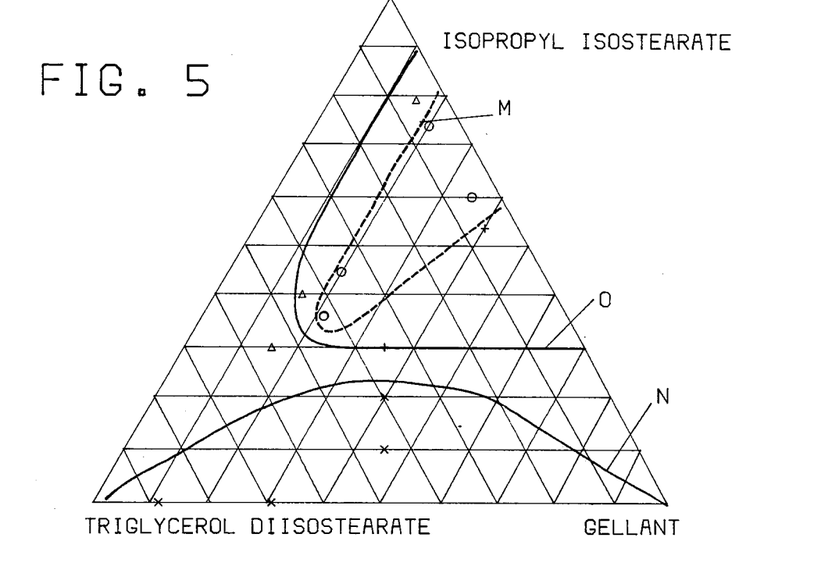

Following the procedure described above, 13 gels were prepared using triglycerol diisostearate as in Example 3 as solvent, isopropyl isostearate as cosolvent and the same ethylene - vinyl acetate copolymers as in Example 1 as gellant. The results are displayed in FIG. 5 using the same symbols as in FIG. 1. The region bounded by line M was determined to contain the "interesting" gels as in Example 1 and the region below line N was determined to contain the incompatible mixtures as in Example 1. Line O has been drawn to further include gels marginally either too thin or too thick.

EXAMPLE 6

Figure 6:
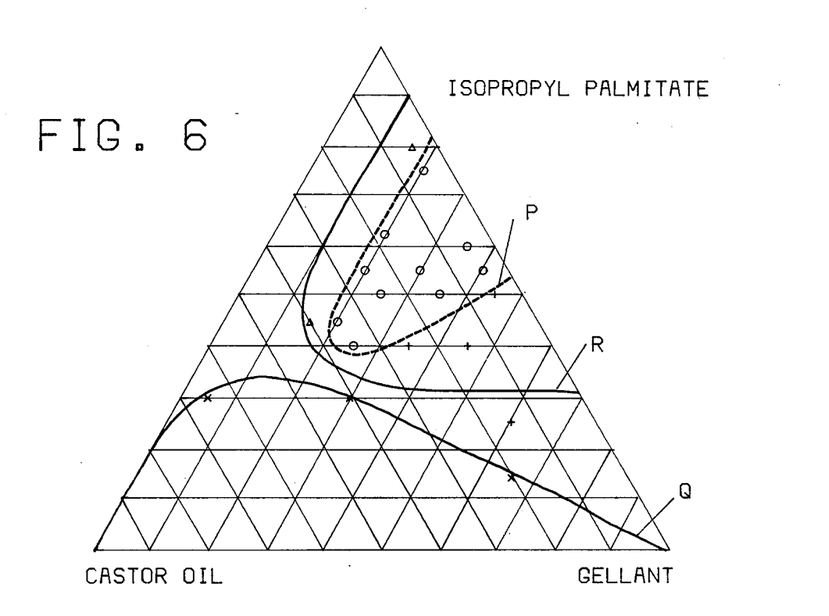

Following the procedure described above, 19 gels were prepared using castor oil as solvent, isopropyl palmitate as cosolvent and the same ethylene - vinyl acetate copolymers as in Example 1 as gellant. The results are displayed in FIG. 6 using the same symbols as in FIG. 1. The region bounded by line P was determined to contain the "interesting" gels as in Example 1 and the region below line Q was determined to contain the incompatible mixtures as in Example 1. An illustrative "interesting" gel was formed from 40 weight percent copolymer, 20 weight percent castor oil and 40 weight percent isopropyl myristate. Line R has been drawn to further include gels marginally either too thin or too thick.

EXAMPLE 7

Figure 7:
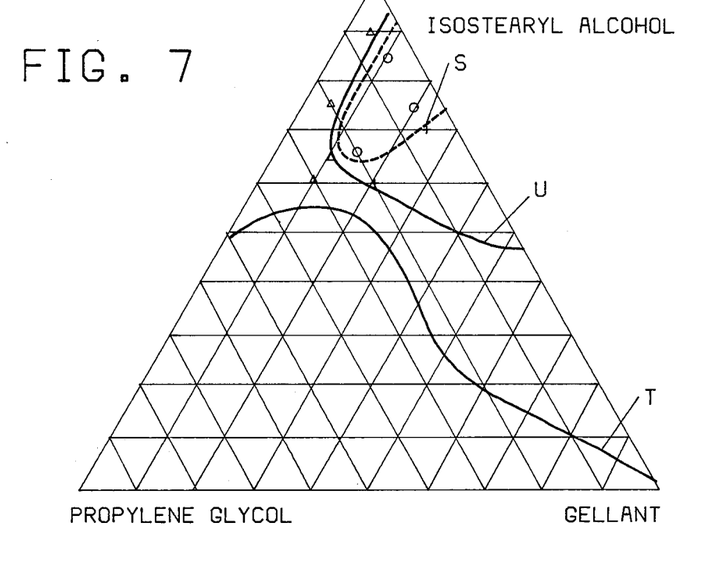

Following the procedure described above, 9 gels were prepared with propylene glycol as solvent, isostearyl alcohol as cosolvent and, as gellant, an ethylene-acrylic acid copolymer having an acid number of 40, a softening point of 108° C., a Brookfield viscosity at 140° C. of about 500 centipoises, and a number average molecular weight about 3000 (from Allied Chemical Corporation as A-C polyethylene copolymer 540). The results are displayed in FIG. 7 using the same symbols as in FIG. 1. The region bounded by line S was determined to contain the "interesting" gels as in Example 1 and the region below line T was determined to contain the incompatible mixtures as in Example 1. Line U has been drawn to further include gels marginally either too thin or too thick.

Figure 8:
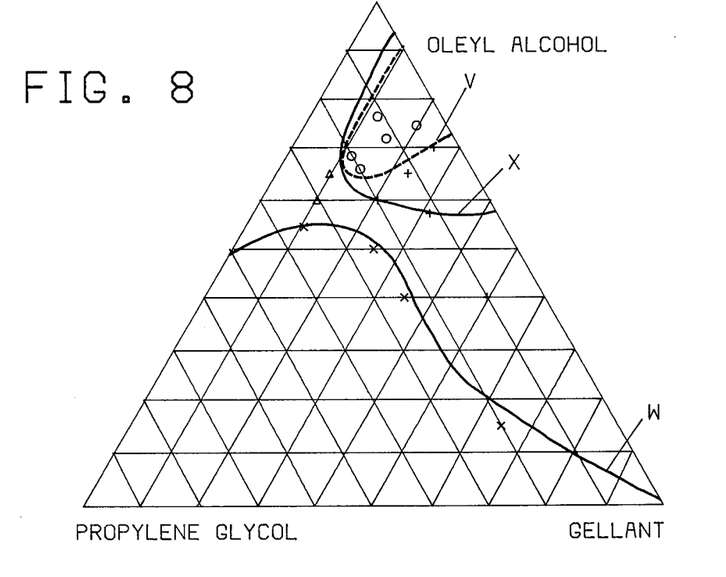

Following the procedure described above, 16 gels were prepared with propylene glycol as solvent, oleyl alcohol as cosolvent and the ethylene-acrylic acid copolymer of Example 7 as gellant. The results are displayed in FIG. 8 using the same symbols as in FIG. 1. The region bounded by line V was determined to contain the "interesting" gels as in Example 1 and the region below line W was determined to contain the incompatible mixtures as in Example 1. Line X has been drawn to further include gels marginally either too thin or too thick.

EXAMPLE 9

Figure 9:
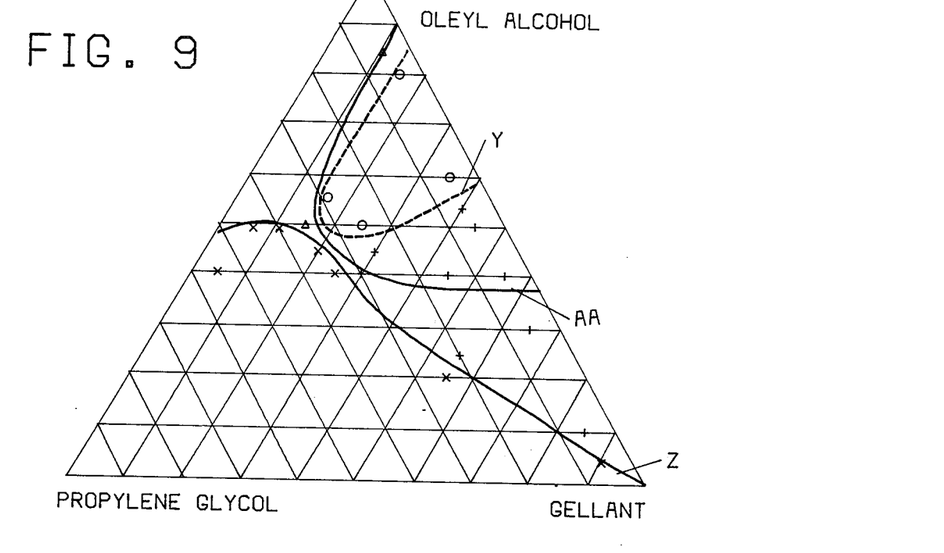

Following the procedure described above, 24 gels were prepared with propylene glycol as solvent, oleyl alcohol as cosolvent and, as gellant, an ethylene-acrylic acid copolymer having an acid number of 75, a softening point of 102° C., a Brookfield viscosity at 140° C. of about 650 centipoises and a number average molecular weight of about 3200 (from Allied Chemical Corporation as A-C polyethylene copolymer 580). The results are displayed in FIG. 9 using the same symbols as in FIG. 1. The region bounded by line Y was determined to contain the "interesting" gels as in Example 1 and the region below line Z was determined to contain the incompatible mixtures as in Example 1. Line AA has been drawn to further include gels marginally either too thin or too thick.

EXAMPLE 10

Figure 10:
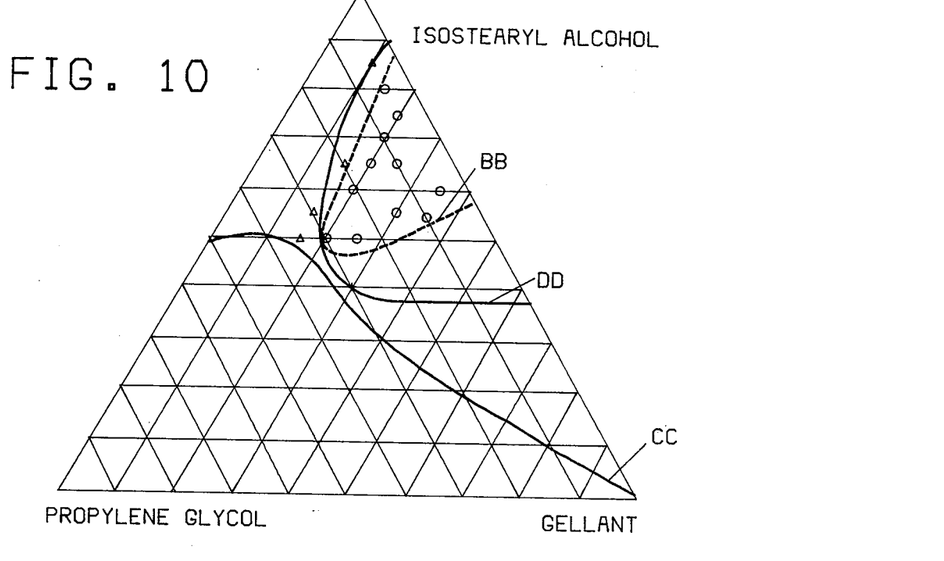

Following the procedure described above, 16 gels were prepared with propylene glycol as solvent, isostearyl alcohol as cosolvent and the ethylene - acrylic acid copolymer of Example 9 as gellant. The results are displayed in FIG. 10 using the same symbols as in FIG. 1. The region bounded by line BB was determined to contain the "interesting" gels as in Example 1 and the region below line CC was determined to contain the incompatible mixtures as in Example 1. Line DD has been drawn to further include the gels marginally either too thin or too thick.

EXAMPLE 11

Figure 11:
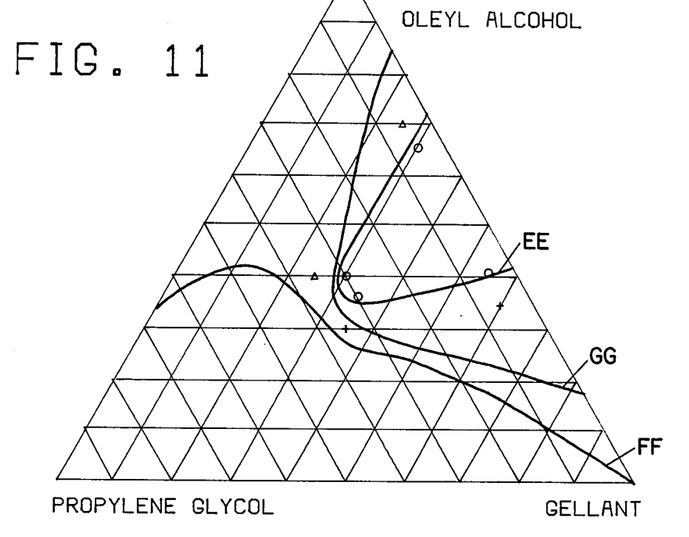

Following the above procedure, 8 gels were prepared with propylene glycol as solvent, oleyl alcohol as cosolvent and, as gellant, an ethylene-acrylic acid copolymer having an acid number of 120, a softening point of 90° C., a Brookfield viscosity at 140° C. of about 700 centipoises and a number average molecular weight of about 3500 (from Allied Chemical Corporation as A-C Polyethylene Copolymer 5120). The results are displayed in FIG. 11 using the same symbols as in FIG. 1. The region bounded by line EE was determined to contain the "interesting" gels as in Example 1 and the region below line FF was determined to contain the incompatible mixtures as in Example 1. Line GG has been drawn to further include the gels marginally either too thin or too thick.

EXAMPLE 12—MEDICINAL ANTIFUNGAL OINTMENT

A gel was prepared following the procedure of Example 1-11 from 20 weight percent of the copolymer of Example 1 (A-C Copolymer 400), 55 weight percent isopropyl palmitate as cosolvent and 25 weight % peanut oil as solvent. This combination gave an "interesting" gel as described above. This gel was then used to formulate an antifungal ointment of 24 weight percent zinc oxide, 15 weight percent copolymer, 42 weight percent isopropyl palmitate and 19 weight percent peanut oil.

EXAMPLE 13—MEDICINAL ANTIBACTERIAL OINTMENT

A gel was prepared following the procedure of Examples 1-11 from 20 weight percent of the copolymer of Example 7 (A-C Copolymer 580), 60 weight percent isostearyl alcohol as cosolvent, and 20 weight percent propylene glycol as solvent. This combination produced an "interesting" gel as described above. Active medication of the type soluble in propylene glycol was added at 0.2 weight % in place of a portion of the propylene glycol to a second batch, producing a gel which was both "interesting" in terms of physical properties and contained the medication fully dispersed in the gel.

EXAMPLES 14-22

Starting with the exemplary "interesting" gel of Example 1, several "interesting" gels were prepared using stearyl alcohol in place of part of the copolymer and/or solvent and candelilla wax in place part of the copolymer. Exemplary suitable proportions are shown in Table 1.

TABLE 1

| Example | 14 | 15 | 16 | 17 | 18 | 19 | 20 | 21 | 22 |
|---|---|---|---|---|---|---|---|---|---|
| Copolymer | 45 | 30 | 25 | 25 | 20 | 20 | 15 | 25 | 20 |
| Dow 556 Fluid | 15 | 15 | 20 | 15 | 15 | 25 | 15 | 15 | 15 |
| Isopropyl Myristate | 40 | 40 | 40 | 40 | 40 | 40 | 50 | 40 | 40 |
| Stearyl Alcohol |  | 15 | 15 | 20 | 25 | 15 | 20 | 15 | 15 |
| Candelilla Wax |  |  |  |  |  |  |  | 5 | 10 |

When the gels of Examples 14-22 were prepared, all nine appeared compatable, somewhat hard gels initially. Examples 14, 21 and 22 remained good gels after four weeks. Examples 15-20, however, indicated instability within four weeks due to migration of the gellant or the stearyl alcohol. It is believed that these latter gels could be improved by lowering the content of Dow 556 Fluid to about 10 percent and correspondingly increasing the content of isopropyl myristate.

EXAMPLES 23-27

The exemplary "interesting" gel of Example 6, containing 40 weight percent copolymer (A-C Copolymer 400), 20 weight percent castor oil and 40 weight percent isopropyl myristate was varied by substituting beeswax, stearyl alcohol and glycerol monostearate for some of the copolymer and in some cases for a part of the castor oil. Exemplary suitable proportions are shown in Table 2.

TABLE 2

| Examples | 23 | 24 | 25 | 26 | 27 |
|---|---|---|---|---|---|
| Copolymer | 40 | 30 | 30 | 15 | 15 |
| Castor Oil | 20 | 15 | 15 | 20 | 20 |
| Isopropyl Myristate | 40 | 40 | 40 | 40 | 50 |
| Beeswax | | 15 | | | |
| Stearyl Alcohol | | | 15 | | |
| Gycerol Monostearate | | | | 25 | 15 |

TABLE 3

| Material | Tradename | Weight % | Source |
|---|---|---|---|
| *Oil Phase* | | | |
| Ethylene Homopolymer | A-C Polyethylene 617 | 1.0 | Allied Chemical Corporation |
| Ethylene Copolymer | A-C Copolymer 540 | 1.0 | Allied Chemical Corporation |
| Mineral Oil | Carnation | 5.0 | Witco |
| Polyphenyl methyl-siloxane Oil | Dow 556 Fluid | 1.0 | Dow Corning Corporation |
| Propylene Glycol Dipelargonate | | 10.5 | Malmstrom Chemicals |
| | Hydroxyol | 2.0 | Malmstrom Chemicals |
| | Ethoxyol 24 | 1.0 | Malmstrom Chemicals |
| Emulsifier | Arlacel 60 | 1.3 | ICI, Atlas Chemical Division |
| Nominic Emulsifer | Tween 60 | 1.8 | ICI, Atlas Chemical Division |
| | Propyl-p hydroxybenzoate | 0.1 | Inolex |
| | | 24.7 | |
| *Water Phase* | | | |
| | Sorbitol (70%) | 5.0 | ICI, Atlas Chemical Division |
| Thickening Agent | Carbopol 940 | 0.75 | B. F. Goodrich Chemical Company |
| | Germal 115 | 0.4 | Sutton Laboratories |
| | Methyl-p-hydroxybenzoate | 0.2 | Inolex |
| Triethanolamine | | 0.75 | |
| Water | | 68.3 | |
| | | 75.4 | |

EXAMPLE 28—TWO PHASE OIL IN WATER CREAM

The ingredients shown in Table 3 were mixed into a gel found of an oil-in-water emulsion. The oil phase ingredients were mixed and heated at 80°–90° C. with slow agitation. The water phase ingredients were prepared by dispering the thickening agent in water and adding the remaining ingredients except triethanolamine and heating to 80°–90° C. The two phases were then mixed and sheared in a homomixer. With mixing continuing, the temperature was lowered to 40° C., triethanolamine was added and the mixture was cooled to 30° C. In practice one would then add perfume, de-aerate and package as a skin-care cream.

It should be appreciated that the ethylene homopolymer and ethylene copolymer are both gellants and together constitute about 8 weight percent of the oil phase, with the copolymer being 50 weight percent of the total gellant. The oil phase of the system was prepared by superimposing a group of emulsifiers and other additives onto a suitable point in a system like Example 1 with propylene glycol dipelargonate replacing isopropyl myristate as the cosolvent.

What is claimed is:

1. A stable, compatible thixotropic gel composition having in the oil phase between about 5 and about 60 weight % gellant, between about 5 and about 50 weight % of a solvent incompatible at room temperature with the gellant and between about 20 and about 90 mole % of a cosolvent compatible with both the gellant and the solvent, at least 25 weight % of said gellant being a copolymer having between about 40 and about 96 mole % ethylene monomer and between about 4 and about 60 mole % of a comonomer selected from the group consisting of acrylic acid, methacrylic acid, ethacrylic acid, esterified acrylic acid, vinyl acetate, vinyl formate, vinyl propionate and mixtures thereof, said copolymer having a number average molecular weight between about 500 and about 10,000, said copolymer being present in a proportion great enough to maintain said gel composition stable from 10° to 50° C.

2. The gel composition of claim 1 wherein said copolymer has a number average molecular weight between about 1000 and about 5000.

3. The gel composition of claim 2 wherein said copolymer has a number average molecular weight between about 2000 and about 4000.

4. The gel composition of claim 2 wherein said copolymer is a copolymer of between about 5 and above 50 mole % vinyl acetate and between about 50 and about 95 mole % ethylene.

5. The gel composition of claim 2 wherein said copolymer has an acid number between about 30 and about 150.

6. The gel composition of claim 2 wherein said comonomer is vinyl acetate.

7. The gel composition of claim 2 wherein said comonomer is acrylic acid.

8. The gel composition of claim 1 wherein said cosolvent is selected from the group consisting of fatty alcohols of 6–20 carbons, fatty acids of 6–20 carbons, fatty esters formed from an alcohol of 1–12 carbons and an acid of 6–24 carbons, aliphatic hydrocarbons of 6–10 carbons, aromatic hydrocarbons of 6–10 carbon and mixtures thereof, said cosolvent having at most one olefinic double bond.

9. The gel composition of claim 1 wherein said cosolvent is selected from the group consisting of saturated fatty alcohols of 14–18 carbons, saturated fatty acids of 14–18 carbons, saturated fatty esters formed from an alcohol of 1–8 carbons and an acid of 14–18 carbons, aromatic hydrocarbons of 6–10 carbons and mixtures thereof.

10. The gel composition of claim 1 wherein the copolymer is a copolymer of about 86 mole % ethylene and 14 mole % vinyl acetate with a number average molecular weight about 3500.

11. The gel composition of claim 10 containing in the oil phase said copolymer, isopropyl myristate and silicone oil in proportions within the region bonded by line A in FIG. 1.

12. The gel composition of claim 10 containing in the oil phase said copolymer, isopropyl myristate and silicone oil in proportions within the region bounded by line C in FIG. 1.

13. The gel composition of claim 10 containing in the oil phase said copolymers, isopropyl myristate and silicone oil in proportions within the region bounded by line D in FIG. 2.

14. The gel composition of clim 10 containing the oil phase said copolymer, isopropyl myristate and silicone oil in proportions within the region bounded by line F in FIG. 2.

15. The gel composition of claim 10 containing in the oil phase said copolymer, butyl stearate and castor oil in proportions within the region bounded by line G in FIG. 3.

16. The gel composition of claim 10 containing in the oil phase said copolymer, butyl stearate and castor oil in proportions within the region bounded by line I in FIG. 3.

17. The gel composition of claim 10 containing in the oil phase said copolymer, butyl stearate and castor oil proportions within the region bounded by line J in FIG. 4.

18. The gel composition of claim 10 containing in the oil phase said copolymer, butyl stearate and castor oil proportions within the region bounded by line L in FIG. 4.

19. The gel composition of claim 10 containing in the oil phase said copolymer, isopropyl isosterate and triglycerol diisostearate in proportions within the region bounded by line M in FIG. 5.

20. The gel composition of claim 10 containing in the oil phase said copolymer, isopropyl isostearate and triglycerol diisostearate in proportions within the region bounded by line O in FIG. 5.

21. The gel composition of claim 10 containing in the oil phase said copolymer, isopropyl palmitate and castor oil in proportions within the region bounded by line P in FIG. 6.

22. The gel composition of claim 10 containing in the oil phase said copolymer, isopropyl palmitate and castor oil in proportions within the region bounded by line R in FIG. 6.

23. The gel composition of claim 1 wherein said copolymer is a copolymer of ethylene and said acrylic acid having an acid number about 40 and a number average molecular weight about 3000.

24. The gel composition of claim 23 having in the oil phase said copolymer, isostearyl alcohol and proplene glycol in proportions within the region bounded by line S in FIG. 7.

25. The gel composition of claim 23 having in the oil phase said copolymer, isostearyl alcohol and propylene glycol in proportions within the region bounded by line U in FIG. 7.

26. The gel composition of claim 23 having in the oil phase said copolymer, oleyl alcohol and propylene glycol in proportions within the region bounded by line V in FIG. 8.

27. The gel composition of claim 23 having in the oil phase said copolymer, oleyl alcohol and propylene glycol in proportions within the region bounded by line X in FIG. 8.

28. The gel composition of claim 1 wherein the copolymer is a copolymer of ethylene and acrylic acid having an acid number about 75 and a number average molecular weight about 3200.

29. The gel composition of claim 28 having in the oil phase said copolymer, oleyl alcohol and propylene glycol in proportions within the region bounded by line Y in FIG. 9.

30. The gel composition of claim 28 having in the oil phase said copolymer, oleyl alcohol and propylene glycol in proportions within the region bounded by line AA in FIG. 9.

31. The gel composition of claim 28 having in the oil phase said copolymer, isostearyl alcohol and propylene glycol in proportions within the region bounded by line BB in FIG. 10.

32. The gel composition of claim 28 having in the oil phase said copolymer, isostearyl alcohol and propylene glycol in proportions within the region bounded by line DD in FIG. 10.

33. The gel composition of claim 1 wherein said copolymer is a copolymer of ethylene and acrylic acid having an acid number about 120 and a number average molecular weight about 3500.

34. The gel composition of claim 33 having in the oil phase said copolymer, oleyl alcohol and propylene glycol in proportions within the region bounded by line EE in FIG. 11.

35. The gel composition of claim 33 having in the oil phase said copolymer, oleyl alcohol and propylene glycol in proportions within the region bounded by line GG in FIG. 11.

* * * * *